US006659945B2

United States Patent
Ball et al.

(10) Patent No.: US 6,659,945 B2
(45) Date of Patent: Dec. 9, 2003

(54) SELF RETAINING RETRACTOR RING (75) Inventors: Robert Ball, Winona Lake, IN (US); Carl Basamania, Chapel Hill, NC (US); Keith McGrath, Warsaw, IN (US); Thomas May, Wrentham, MA (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/897,651

(22) Filed: Jun. 29, 2001

(65) Prior Publication Data

US 2003/0004401 A1 Jan. 2, 2003

(51) Int. Cl.[7] ................................................ A61B 17/02
(52) U.S. Cl. ...................................................... 600/233
(58) Field of Search ................................. 600/201, 208, 600/215, 227, 229, 231, 233, 234, 217

(56) References Cited

U.S. PATENT DOCUMENTS

| 2,384,304 | A | * | 9/1945 | Helfrick ...................... 600/233 |
| 2,845,925 | A | * | 8/1958 | Jayle .......................... 600/233 |
| 3,038,468 | A | * | 6/1962 | Raeuchle .................... 600/223 |
| 3,749,088 | A | | 7/1973 | Kohlmann |
| 3,965,890 | A | | 6/1976 | Gauthier |
| 3,998,217 | A | | 12/1976 | Trumbull et al. |
| 4,010,741 | A | | 3/1977 | Gauthier |
| 4,099,521 | A | | 7/1978 | Nestor et al. |
| 4,254,763 | A | | 3/1981 | McCready et al. |
| 4,274,398 | A | | 6/1981 | Scott, Jr. |
| 4,337,762 | A | | 7/1982 | Gauthier |
| 4,421,107 | A | | 12/1983 | Estes et al. |
| 4,434,791 | A | * | 3/1984 | Darnell ....................... 600/234 |
| 4,457,300 | A | | 7/1984 | Budde |
| 5,284,129 | A | | 2/1994 | Agbodoe et al. ............ 606/130 |
| 5,496,319 | A | | 3/1996 | Allard et al. .................. 606/56 |
| 5,529,358 | A | | 6/1996 | Dinkler et al. .............. 600/233 |
| 5,769,783 | A | | 6/1998 | Fowler ......................... 600/226 |
| 5,876,333 | A | | 3/1999 | Bigliani et al. ............. 600/231 |
| 5,928,139 | A | | 7/1999 | Koros et al. ................. 600/205 |
| 5,947,895 | A | | 9/1999 | Warner ........................ 600/204 |
| 5,951,467 | A | * | 9/1999 | Picha et al. ................. 600/206 |
| 6,030,340 | A | | 2/2000 | Maffei et al. ............... 600/233 |
| 6,190,312 | B1 | * | 2/2001 | Fowler, Jr. .................. 600/233 |
| 6,398,726 | B1 | * | 6/2002 | Ramans et al. ............. 600/235 |

FOREIGN PATENT DOCUMENTS

| FR | 1605461 | 5/1976 |
| WO | WO 99 21484 | 5/1999 |

* cited by examiner

Primary Examiner—Cary E. O'Connor
(74) Attorney, Agent, or Firm—Maginot, Moore & Beck (57) ABSTRACT

An adjustable self retaining retractor ring assembly is provided. The self retaining retractor ring assembly is formed from two half-rings connected together by hinges to form a 360° enclosure or ring. The hinges allow the two half-rings to bend or pivot 180° relative to a plane of the ring. One of the hinges includes a positionable locking mechanism to lock or set the angular orientation of the two half-rings relative to each other. In this manner, fixed angles for the half-rings can be selected and maintained. Each half-ring includes a plurality of axially protruding pegs or posts (relative to a plane of the half-ring) positioned thereabout. The posts are shaped to releasably accept retractors and/or ancillary instruments thereon. Additionally, each post preferably includes a slot configured to allow for the locking of suture material therein.

18 Claims, 8 Drawing Sheets

SELF RETAINING RETRACTOR RING

TECHNICAL FIELD OF THE INVENTION

The present invention relates generally to retractors, and more particularly, to a retractor ring assembly.

BACKGROUND OF THE INVENTION

Open and mini-open surgical procedures require a varying amount of instruments for retracting and holding both instruments and the patient's tissue. More particularly, there are many soft tissue surgical procedures, such as about the shoulder for example, that require an open or mini-open technique, as opposed to an arthroscopic technique. The nature of these open and mini-open procedures typically requires expensive resources (i.e. additional staff such as surgeons and assistants) to assist with retraction by holding the various retraction and/or surgical instruments.

Unfortunately, additional staff is costly, as well as a source of inconsistency for retraction. In view of this, there have been developed various devices to assist the surgeon in retraction positioning and retention during such open and mini-open surgical procedures. One such device known as the Hawkins Bell® system currently marketed by DePuy Orthopaedics, Inc. of Warsaw, Ind., uses a shaft bent into a U-shape that can hold three retractors. Two of the retractors must be positioned at the ends of the shaft, and the third retractor is attached to the shaft through a small locking block. The primary disadvantages of this system are: 1) that attachments such as retractors cannot be positioned anywhere (360°) surrounding the wound (opening); 2) the system is not adaptable to a patient's anatomy; and 3) sutures cannot be retracted using the system. Since the shaft cannot bend, this eliminates the ability to adjust the A/P direction of retraction, as well as S/I and M/L.

Other devices for retraction holding have been developed such as self-retracting forceps. These forceps allow the attachment of retractor blades to the ends of the forceps. The forceps, thus opening the wound, can thus separate the blades. A disadvantage to these devices is the lack of flexibility, i.e. there is no control over the direction of retraction. Additionally, only two retractors can be mounted to the forceps.

In sum, these previous devices/attempts, however, have lacked the flexibility to be used in a wide variety of applications, without creating more nuisance than assistance.

What is therefore needed is a self retaining retractor holder that overcomes one or more of the drawbacks associated with prior art retractor holders. What is also needed is a self retaining retractor ring that is adaptable to the contours of a patient. What is further needed is a self retaining retractor ring that includes functionality in addition to holding retractors.

SUMMARY OF THE INVENTION

The present invention is a retractor holding assembly and, particularly a retractor ring assembly. The retractor ring assembly is articulatable into various angled positions and preferably defines a 360° enclosure. The retractor ring assembly also includes pegs that surround the incision (enclosure) by 360°, and have suture retaining slots.

In accordance with another embodiment of the present invention, there is provided a retraction retaining device. The retraction retaining device includes a first ring portion defining a first end and a second end, a first plurality of posts disposed on the first ring portion with each post configured to retain an instrument, a second ring portion defining a first end and a second end, and a second plurality of posts disposed on the second ring portion with each post configured to retain an instrument. The retaining device further includes a first hinge coupled to and between the first ends, and a second hinge coupled to and between the second ends. The first and second hinges are configured to allow various angular positions of the first and second ring portions. In accordance with a further embodiment of the present invention, there is provided a retraction retaining device having an articulating ring, and a plurality of posts disposed on a surface of the articulating ring with each post configured to retain a surgical instrument.

In accordance with yet another embodiment of the present invention, there is provided a method of retracting a surgical opening. The method includes the steps of: (a) providing a hinged ring defining an opening therein and having a plurality of posts disposed on an upper surface thereof; (b) articulating the hinged ring into a particular angular orientation; (c) locking the hinged ring into the particular angular orientation; (d) positioning the opening of the hinged ring over the surgical opening; and (e) attaching a retractor to one of the posts, the retractor operative to retract a portion of the surgical opening.

In still another form, the present invention is a method of retaining a suture during an open surgery. The method includes the steps of: (a) providing a hinged ring defining an opening therein and having a plurality of posts disposed on an upper surface thereof, each one of the plurality of posts having a slot configured to releasably retain a suture; (b) positioning the opening of the hinged ring over the surgical opening; and (c) placing a suture in the slot of a chosen post.

In a yet further form, the present invention is a retraction retaining device having a ring, and a plurality of pegs disposed on an upper surface of the ring and spaced thereon so as to encompass 360° of the ring with each peg configured to releasably retain a surgical instrument.

It is therefore an object of the present invention to provide a new and useful retractor retainer.

It is moreover an object of the present invention to provide an improved retractor retainer.

It is a further object of the present invention to provide a new and useful method of providing retraction during surgery.

It is also an object of the present invention to provide an improved method of retaining a suture during open surgery.

The above and other objects, features, and advantages of the present invention will become apparent from the following description and the attached drawings.

BRIEF DESCRIPTION OF THE DRAWINGS

Corresponding reference characters indicate corresponding parts throughout the several views.

DESCRIPTION OF THE INVENTION

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Figure 1:
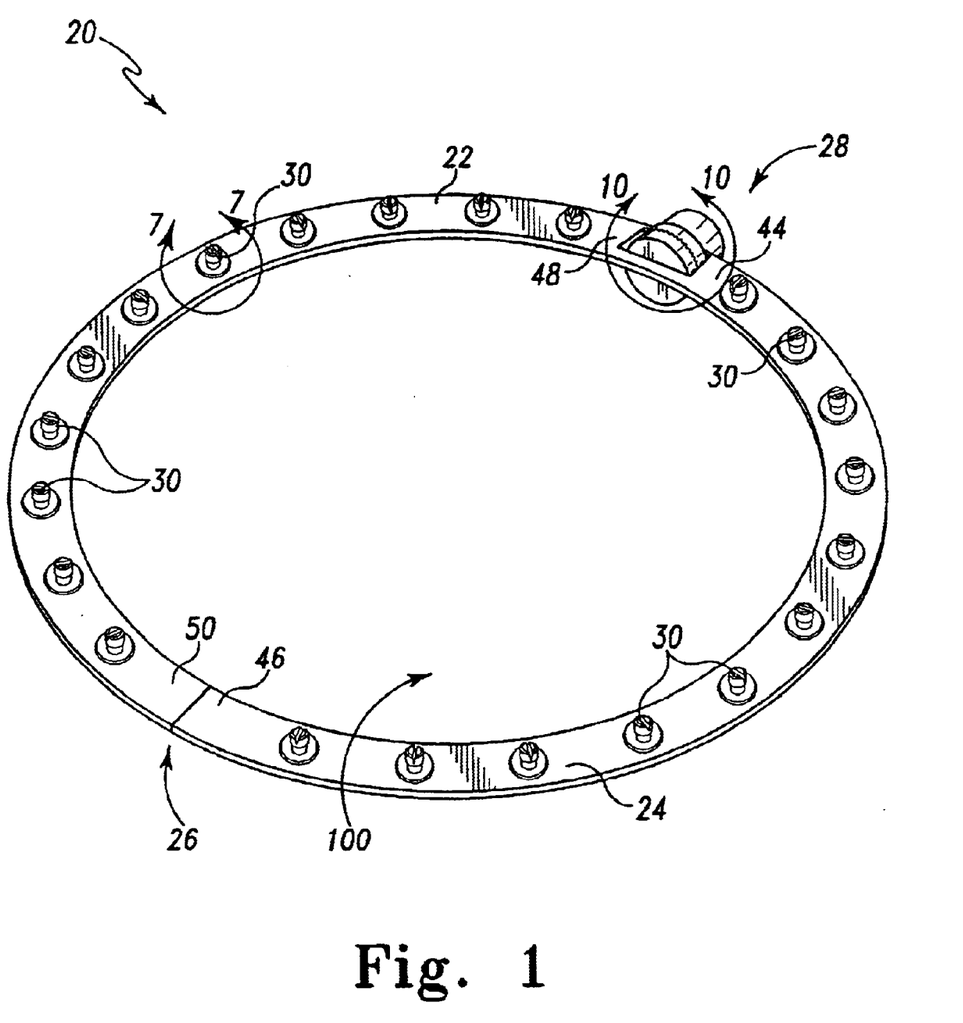
FIG. 1 is a perspective view of a retractor ring assembly in accordance with the principles of the present invention.
Figure 2:
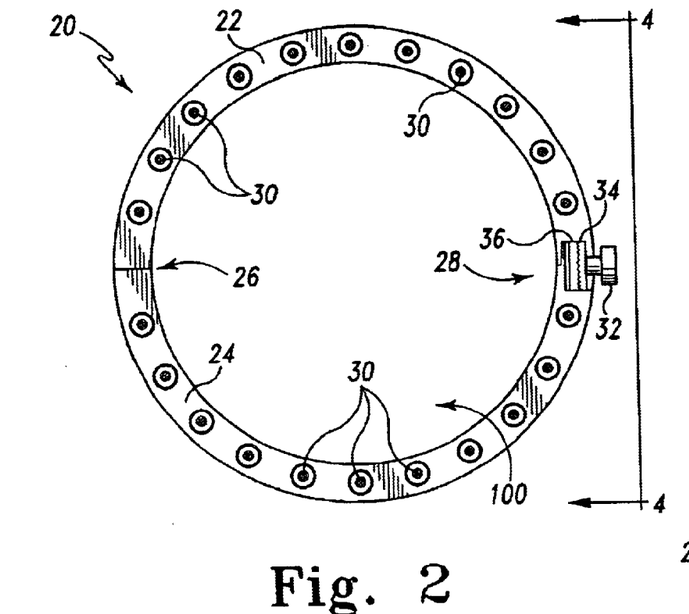
FIG. 2 is a top plan view of the retractor ring assembly of FIG. 1.
Figure 3:
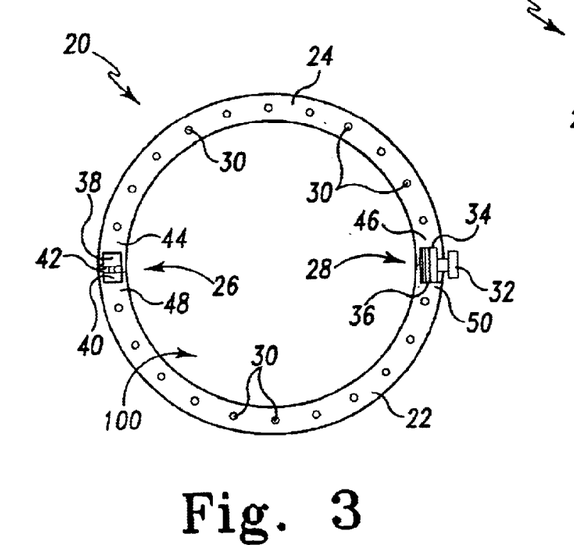
FIG. 3 is a bottom plan view of the retractor ring assembly of FIG. 1.

Referring now to FIGS. 1–3, there is shown a retractor holding or ring assembly, generally designated 20, in accordance with the principles presented herein. The retractor ring assembly 20 includes a first ring portion 22 and a second ring portion 24. The first and second ring portions 22 and 24 are coupled to one another at first respective ends 50 and 46 (see additionally FIGS. 5 and 6) thereof via a first pivot or hinge assembly 26. The first and second ring portions 22 and 24 are coupled to one another at second respective ends 48 and 44 (see additionally FIGS. 5 and 6) thereof via a second pivot or hinge assembly 28.

The first hinge assembly 26 and the second hinge assembly 28 permit the ring assembly 20 to articulate, swing, or pivot. With additional reference to FIG. 4, such articulating is represented by the double-headed arrow. The first and second ring portions 22 and 24 are articulatable into a common plane define by the ring portions 22 (arbitrarily, 0°) and through 180°The first and second ring portions may be positioned into various angles off of the plane (0°). Additionally, the hinge assembly 26 also allows the two ring portions or halves to "shift" along an axis defined by the hinge assembly 26. This permits, in one respect, the lockable hinge assembly 28 to release or unlock for an angle change.

Figure 5:
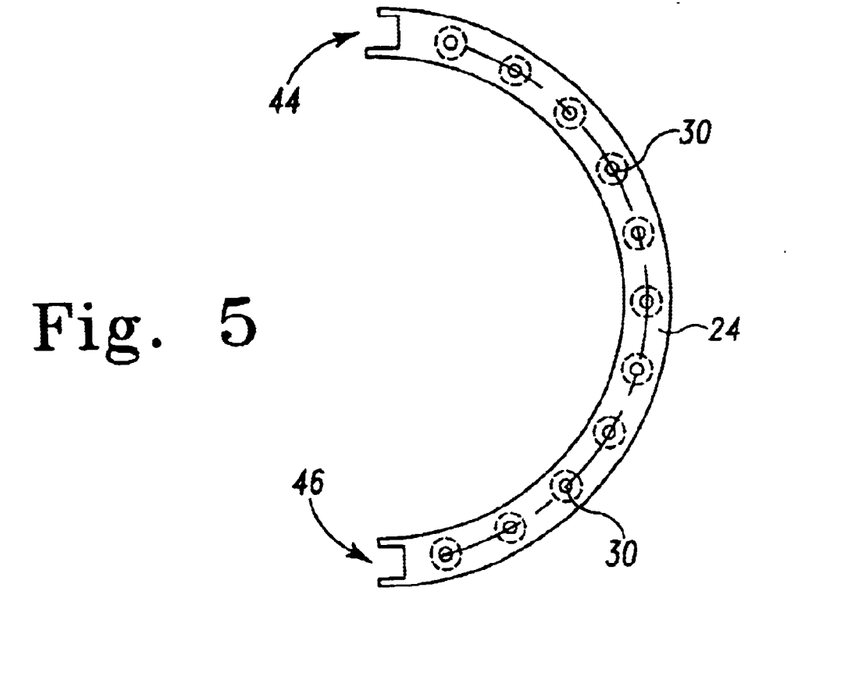
FIG. 5 is a top plan view of a first retractor ring portion of the present retractor ring assembly.
Figure 6:
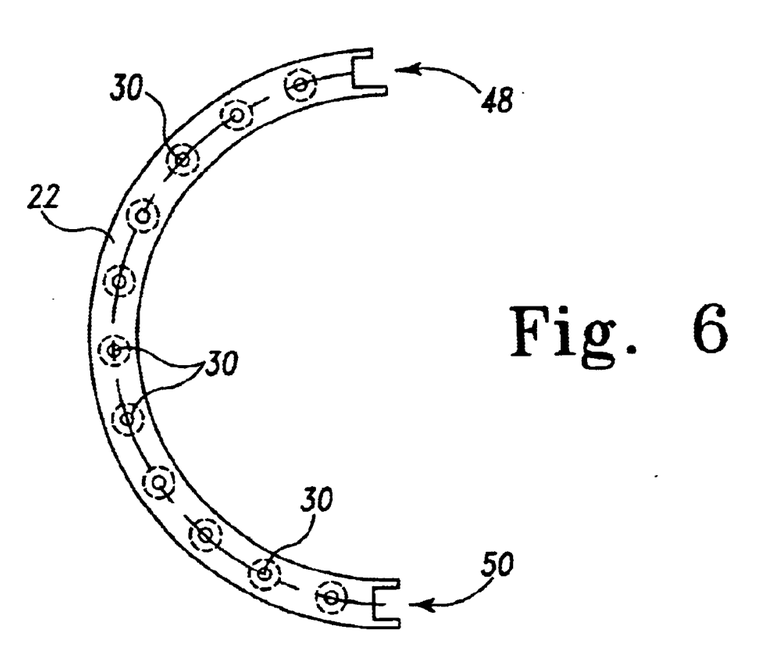
FIG. 6 is a top plan view of a second retractor portion of the present retractor ring assembly.

As best seen in FIGS. 5 and 6, the first and second ring portions 22 and 24 are each of an arcuate shape. More particularly, the first and second ring portions 22 and 24 are preferably relatively flat, semi-circular members such that a ring formed thereby is substantially circular. The first and second arcuate portions 22 and 24 may, however, take other shapes so that the resulting union thereof creates a ring that is oblong, elliptical, or the like. Each ring portion 22 and 24 is preferably made of a suitable metal such as stainless steel, a titanium alloy, or the like. Of course, other suitable material may be used.

The retractor ring assembly 20 further includes a plurality of posts or pegs 30 disposed on a respective upper surface of the first and second ring portions 22 and 24. Each peg is positioned in a bore or hole in the ring portion. The pegs 30 are preferably spaced about each ring portion such that the pegs encompass 360° about an opening 100 defined by the ring portions 22 and 24 when assembled. Further, while twenty-two (22) pegs 30 are shown, any number may suffice. Each peg 30 extends axially outwardly from its respective ring portion.

Figures 7, 8, 9:
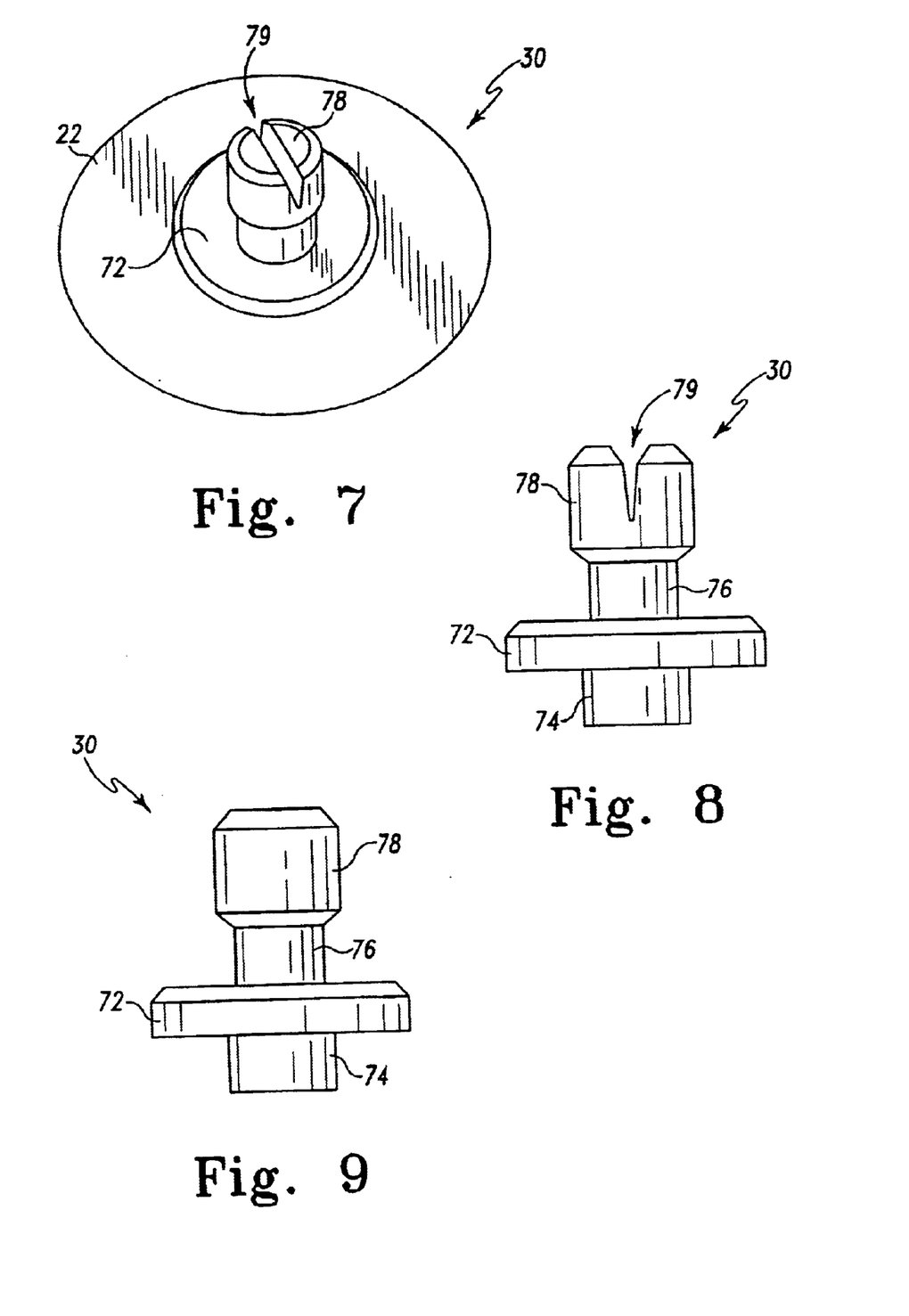
FIG. 7 is an enlarged perspective view of the post of the present retractor ring assembly.
FIG. 8 is an enlarged side view of a post of the present retractor ring assembly.
FIG. 9 is another enlarged side view of the present retractor ring assembly.

Referring to FIGS. 7–9, a peg 30 representative of all pegs 30 is depicted in greater detail. The peg 30 includes a base or seating portion 72 that is adapted to abut the upper surface of the respective ring portion. Extending axially downwardly from the base 72 is a seating post 74 that is received in a bore or hole of a ring portion. Extending axially upwardly from the base 72 is a center post 76. A peg head 78 is positioned on the center post 72. The peg head 78 includes a slot 79. The slot 79 is configured to releaseably retain a suture therein. Additionally and preferably, the slot 79 is radially aligned with a center point of the opening 100 of the ring assembly 20.

The peg 30 is preferably made of a suitable metal such as stainless steel, a titanium alloy, or the like. Each peg 30 is attached to a respective ring portion. Preferably, each slot 79 is tapered so as to enable the slot 79 to retain a portion of a suture from the wound. Each peg 30 is configured to receive and releasably retain an instrument, particularly a surgical instrument, via a complementary hole in the surgical instrument. The surgical instrument is preferably a retractor. Thus, a plurality of surgical instruments are attachable to the retractor ring 20 via the pegs 30.

Figure 4:
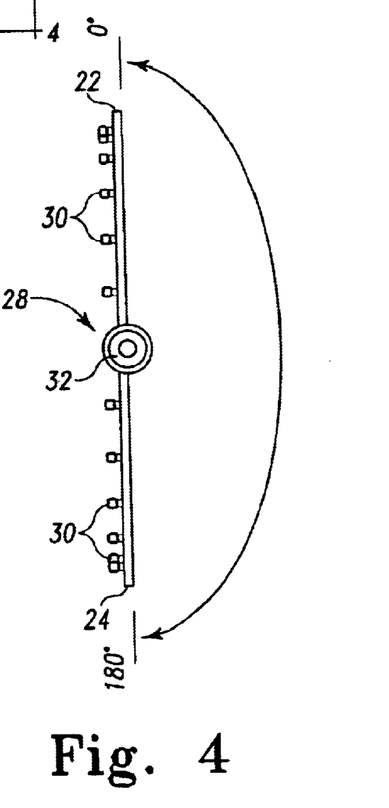
FIG. 4 is a side view of the retractor ring assembly taken along line 4—4 of FIG. 2.

Referring back to FIG. 3, the hinge assembly 26 pivotally couples the end 44 of the ring portion 24 with the end 48 of the ring portion 22. The hinge assembly 26 includes a first hinge portion 38 that is coupled to a second hinge portion 40 via a hinge pin 42. The first hinge portion 38 is fixedly attached to the end 44, while the second hinge portion 48 is fixedly attached to the end 48. The hinge assembly 26 allows the ring portions 22 and 24 to pivot downwardly, but not upwardly with respect to the plane defined by the ring portions (ref. FIG. 4).

The hinge assembly 28 pivotally couples the end 46 of the ring portion 24 with the end 50 of the ring portion 22. The hinge assembly 28 includes a knob 32, a locking washer 34, and a locking screw washer 36. The hinge assembly 28 allows the ring portions 22 and 24 to pivot downwardly, but not upwardly with respect to the plane defined by the ring portions (ref. FIG. 4). Further, the hinge assembly 28 is releasably lockable to releasably fix an angle of articulation of the ring portions 22 and 24. Particularly, the hinge assembly 28 is releasably lockable in discrete steps to fix various angles of orientation of the ring portions 22 and 24. Thus, the ring assembly 20 may be configured to adapt to the contours of a patient when the ring assembly is placed on the patient.

Figure 11:
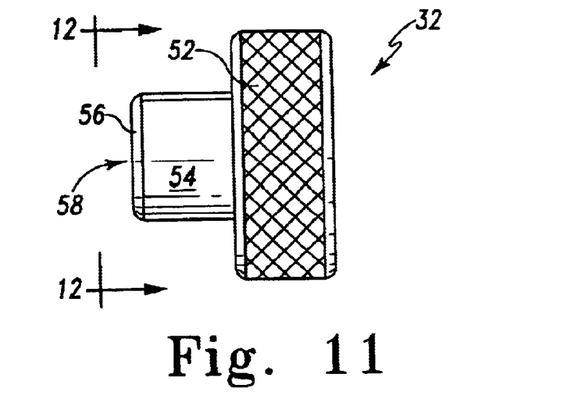
FIG. 11 is an enlarged plan view of an adjustment knob of the adjustment mechanism of the present retractor ring assembly.
Figure 12:
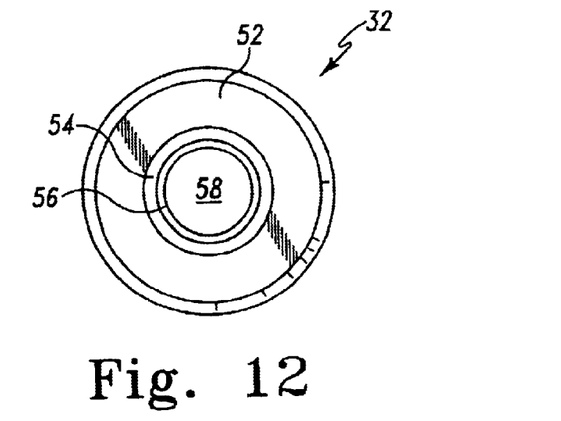
FIG. 12 is a bottom plan view of the retractor ring adjustment assembly of FIG. 11 taken along line 12—12 thereof.

FIGS. 11 and 12 depict the knob 32 of the hinge assembly 28. Initially, the knob 32 is preferably made of a suitable metal such as stainless steel or a titanium alloy. Of course, as with all of the parts of the present invention, other suitable materials may be used. The knob includes a round, knurled head 52 adapted to allow a user to easily grip and rotate the knob 32. Extending from the head 52 is a shaft 54 terminating distal to the head 52 in a beveled portion 56. The shaft 54 defines an interior cavity 58 that is threaded.

Figure 13:
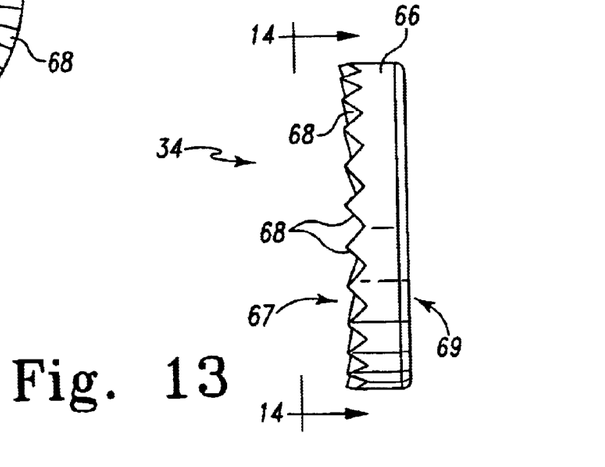
FIG. 13 is an enlarged side view of a lock washer of the adjustment assembly of the present retractor ring assembly.
Figure 14:
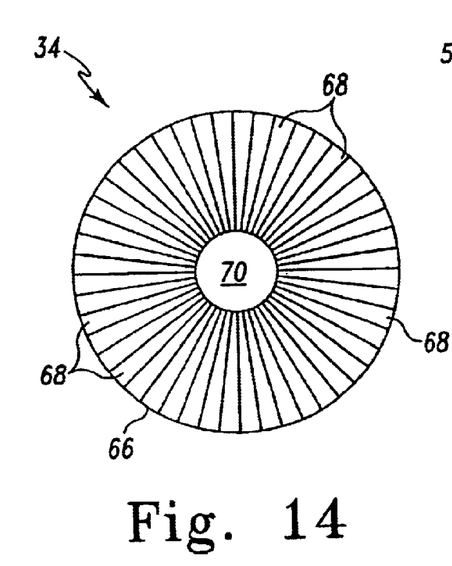
FIG. 14 is an enlarged bottom view of the lock washer of FIG. 13 taken along line 14—14 thereof.

FIGS. 13 and 14 depict the lock washer 34 of the hinge assembly 28. Initially, the lock washer 34 is preferably made of a suitable metal such as stainless steel or a titanium alloy. Other suitable material may also be used. The lock washer 34 includes a washer body 66 having a front side 67 having a plurality of teeth or notches 68 radially, progressively extending from a central bore 70, the tops of which axially extend from central troughs thereof. The lock washer 34 also defines a rear side 69.

The number of teeth 68 may vary according to design preferences, with the number of teeth (i.e. the spacing thereof) defining incremental angles. The incremental angles provide discrete incremental positions or adjustments for the articulation of the ring portions 22 and 24. In a preferred form, the teeth provide 15°increments. Of course, other fixed angle increments may be provided.

Figure 15:
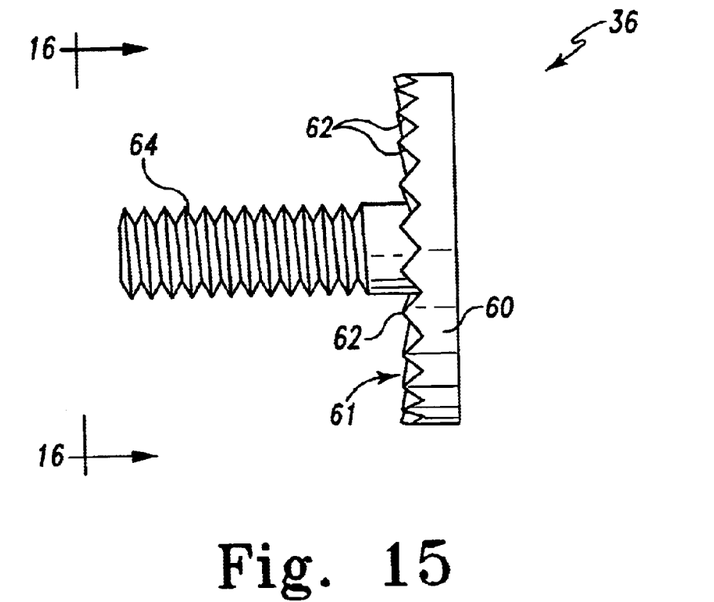
FIG. 15 is an enlarged side view of a locking screw of the adjustment assembly of the present retractor ring assembly.
Figure 16:
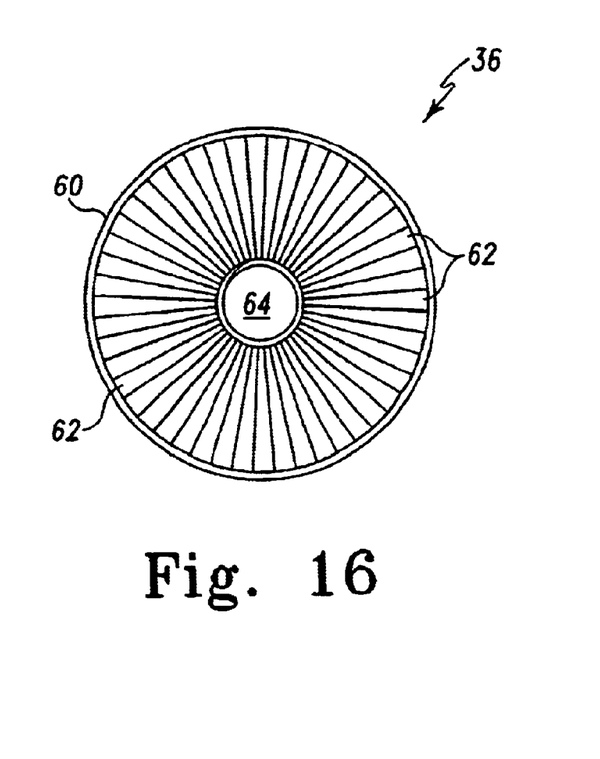
FIG. 16 is an enlarged bottom view of the locking screw of FIG. 15 taken long line 16—16 thereof.

FIGS. 15 and 16 depict the locking screw washer 36. The locking screw washer 36 is again, preferably made of a suitable metal such as stainless steel, a titanium alloy, or the like. The screw washer 36 includes a lock washer body 60 having a front face 61 having a plurality of teeth or notches 62 radially, progressively extending from a screw or threaded shaft 64, the tops of which axially extend from central troughs thereof. The teeth 62 are configured to mesh with the teeth 68 of the lock washer 34. The threaded shaft 64 is adapted to extend through the bore 70 of the lock washer 34 and be threadedly received in the threaded shaft 58 of the knob 32.

Figure 10:
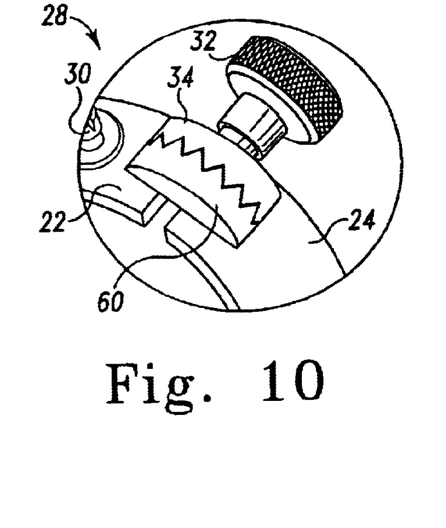
FIG. 10 is an enlarged perspective view of the adjustment mechanism of the present retractor ring assembly.

Referring to FIG. 10, the hinge assembly 28 is shown in greater detail. In particular, the lock washer 60 of the locking screw washer 36 is attached to either the ring portion 22 or the ring portion 24, while the lock washer 34 is attached to the other of the ring portion 22 or ring portion 24. The screw or threaded shaft 64 of the locking screw washer 36 (of which the lock washer portion 60 is seen) extends through the bore 70 of the lock washer 34 and threadedly engages the threaded opening 58 of the knob shaft 54.

Tightening of the knob 32 causes the bevel 56 of the shaft 54 of the knob 32 to abut the rear surface 69 of the lock washer 34. Further tightening causes the teeth 68 of the lock washer 34 to engage the teeth 62 of the lock washer body 60. Since a ring portion is coupled to one of the lock washers 60 and 66, the orientation of the lock washers 60 and 66 relative to each other sets the angle of the ring assembly 20. Loosening of the knob 32 allows at least one of the lock washers 60 and 66 to rotate relative to the other, or both, to reposition the ring portions 22 and 24 into another angle.

Figure 17:
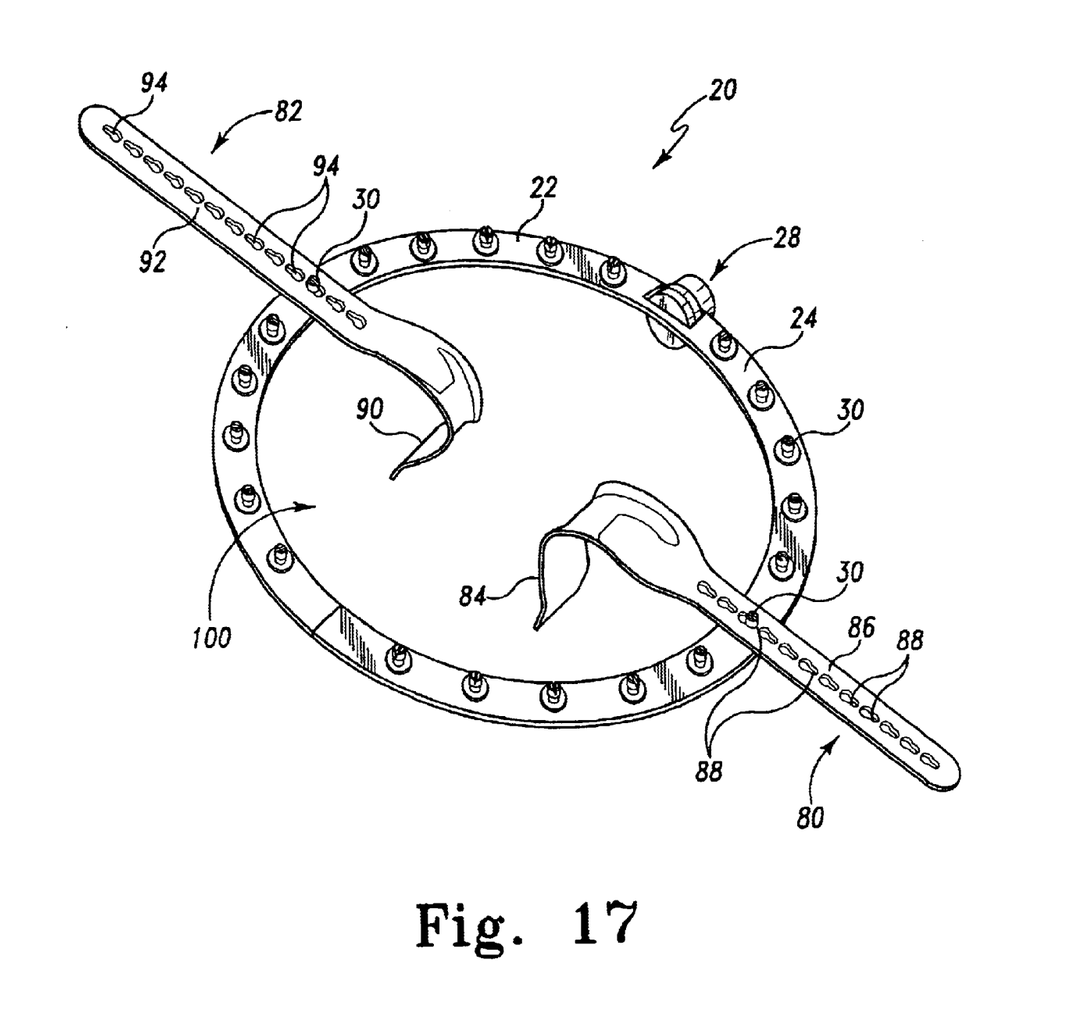
FIG. 17 is a perspective view of the present retractor ring holding a pair of deltoid retractors.

Referring to FIG. 17, the retractor ring assembly 20 is shown having a first retractor 80 attached thereto, and a second retractor 82 attached thereto. The present invention provides the retractors 80 and 82 (and in general all surgical instruments attached thereto) in a radial loading pattern anywhere in the 360° range of pegs 30. In a manner similar to any instrument that is releasably attachable to the ring assembly 20, the retractor 80 includes a plurality of bores 88 that are configured to accept a peg 30 therein. The bores 88 are positioned along a shaft 86 of the retractor 80. In this manner, the retractor 80 may be arcuately positionable on any peg 30 and is radially inwardly or outwardly adjustable for the particular surgical opening. The blade 84 of the retractor 80 may thus be inwardly or outwardly positionable to hold open the surgical opening.

The retractor 82 likewise includes a plurality of bores 94 that are configured to accept a peg 30 therein. The bores 94 are positioned along a shaft 92 of the retractor 82. In this manner, the retractor 82 may be arcuately positionable on any peg 30 and is radially inwardly or outwardly adjustable for the particular surgical opening. The blade 90 of the retractor 82 may thus be inwardly or outwardly positionable to hold open the surgical opening. It should be appreciated that more than two instruments may be supported by the present ring assembly 20, limited only by the amount of room around the ring.

It should further be appreciated that while the ring portions 22 and 24 are shown in FIG. 17 in a 0° position, they may be angled as shown and described herein in accordance with the principles of the present invention. The ring assembly 20 further defines an opening 100 that is situated over the surgical opening (or area where a surgical opening is to be made) during use.

It should be appreciated that variations on the above are possible. Particularly, with respect to the pegs 30 and corresponding bores of an instrument, the pegs and bores may be reversed. The pegs may be formed as part of the instrument rather than holes, in which case the holes may be formed on the ring portions rather than pegs. Further, the locking hinge may take many forms other than that shown. The locking hinge may be spring-loaded and/or provide for a quick-change of angles, or for biasing the ring assembly 20 into a "normal" position.

In addition, since the present ring assembly 20 is very stable once installed, the ring assembly 20 may be used as a baseline alignment device. Thus, various measurements and the like may be made from the ring assembly 20, as well as the positioning of other instruments/procedures independent of the ring assembly 20.

Operation of the Present Invention

Figure 18:
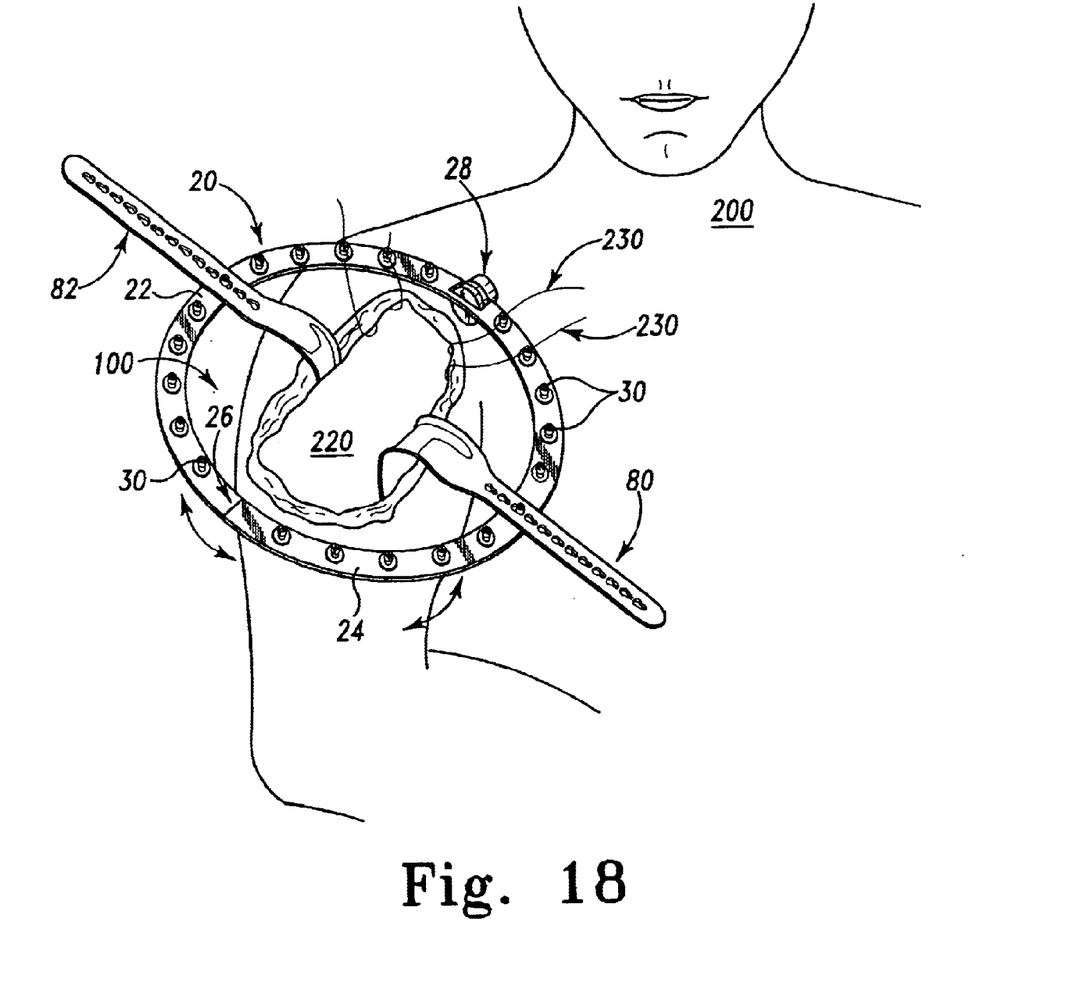
FIG. 18 is a perspective view of the present retaining ring assembly positioned over a patient and holding a pair of retractors of an incision of a patient.

In operation, and referring to FIG. 18, the ring assembly 20 is placed on a patient 200, particularly such that the opening 100 of the ring assembly 20 is over a surgical opening or wound 220 of the patient 200. The angular orientation of the ring portions 22 and 24 are set such that each ring portion contacts the patient. In this manner, the ring assembly 20 almost totally rests upon the patient. The retractors 80 and 82 are positioned on the ring assembly 20 so as to maintain the incision in an open position.

Further, as shown in FIG. 18, sutures 230 that extend from the incision 220 may be retained by the slots 79 of the pegs 30. The double-headed arrows indicate that the ring portions 22 and 24 articulate or can be angled appropriately for the patient 200.

The present invention is useful during shoulder surgery, such as arthroplasty or the like, as well as other surgical procedures where retraction of an incision, surgical opening, or would is required. As well, although not shown in FIG. 18, the present ring assembly 20 may hold other instruments.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected.

There are a plurality of advantages of the present invention arising from the various features of the retractor described herein. It will be noted that alternative embodiments of the retractor of the present invention may not include all of the features described, yet still benefit from at least some of the advantages of such features. Those of ordinary skill in the art may readily devise their own implementations of a retractor that incorporate one or more of the features of the present invention and fall within the spirit and scope of the present invention as defined by the appended claims.

What is claimed is:

1. A retraction retaining device comprising:
   a first ring portion having an upper surface and defining a first end and a second end;
   a first plurality of posts disposed on said upper surface of said first ring portion, each post configured to retain an instrument;
   a second ring portion having an upper surface and defining a first end and a second end, said first ring portion and said second ring portion defining a plane;
   a second plurality of posts disposed on said upper surface of said second ring portion, each post configured to retain an instrument;
   a first hinge coupled to and between said first ends; and
   a second hinge coupled to and between said second ends;
   said first and second hinges configured to:
      allow said first and second ring portions to pivot downwardly with respect to the plane; and
      prevent said first and second ring portions from pivoting upwardly with respect to the plane.

2. The retraction retaining device of claim 1, wherein said first and second hinges are configured to allow various angular positions extending from said plane of said first and second ring portions through 180°.

3. The retraction retaining device of claim 1, wherein said first and second hinges are configured to allow various angular positions extending from said plane of said first and second ring portions through 180° in discrete increments.

4. The retraction retaining device of claim 3, wherein said discrete increments comprise 15° increments.

5. The retraction retaining device of claim 1, wherein one of said first and second hinges is releasably lockable into various angular positions.

6. The retraction retaining device of claim 5, wherein said releasably lockable hinge is operative to releasably lock said first and second ring portions through 180° in discrete increments.

7. The retraction retaining device of claim 6, wherein said discrete increments comprise 15° increments.

8. The retraction retaining device of claim 7, wherein said releasably lockable hinge includes teeth defining said discrete 15° increments.

9. The retraction retaining device of claim 1, wherein said first and second ring portions define, in one angular position thereof, a circular ring.

10. A retraction retaining device comprising:
    a first ring portion defining a first end and a second end;
    a second ring portion defining a first end and a second end;
    a lockable hinge coupled to and between said first ends; and
    an unlockable hinge coupled to and between said second ends,
    wherein at least one of said first ring portion and said second ring portion is articulatable into various angular positions extending from a plane (0°) of said first and second ring portions through 180° in discrete increments.

11. The retraction retaining device of claim 10, wherein at least one of said first ring portion and said second ring portion is articulatable in 15° discrete increments.

12. A method of retracting a surgical opening comprising the steps of:
    providing a hinged ring defining an opening therein and having a plurality of posts disposed on an upper surface thereof, said hinged ring including a first ring portion, a second ring portion and a hinge coupled to each of said first ring portion and said second ring portion, said hinge defining an axis;
    shifting at least one of said first ring portion and said second ring portion alone said axis of said hinge;
    articulating the hinged ring into a particular angular orientation;
    locking the hinged ring into the particular angular orientation;
    positioning the opening of the hinged ring over the surgical opening; and
    attaching a retractor to one of the posts, the retractor operative to retract a portion of the surgical opening,
    wherein the step of articulating the hinged ring into a particular angular orientation includes articulating the hinged ring through predetermined increments.

13. The method of claim 12, wherein the predetermined increments comprises 15°.

14. A retraction retaining device comprising:
    a first ring portion defining a first end and a second end;
    a second ring portion defining a first end and a second end, said first ring portion and said second ring portion defining a plane;
    a plurality of pegs disposed on at least one of an upper surface of said first ring and an upper surface of said second ring, each peg configured to releasably retain a surgical instrument;
    a first hinge coupled to and between said first ends; and
    a second hinge coupled to and between said second ends;
    said first and second hinges configured to allow either of said first and second ring portions to pivot downwardly with respect to the plane in an arc of greater than 90°,
    wherein each one of said plurality of pegs includes a slot,
    wherein said first and second ring portions are hinged so as to be articulatable into various angular positions, and
    wherein said first and second ring portions are hinged so as to be articulatable into the various angular positions via discrete increments.

15. The retraction retaining device of claim 14, wherein said discrete increments is 15°.

16. A surgical retractor assembly, comprising:
    a first retractor segment having (i) a first upper surface and a first lower patient facing surface, and (ii) a first plurality of posts extending upwardly from said first upper surface;
    a second retractor segment having (i) a second upper surface and a second lower patient facing surface, and (ii) a second plurality of posts extending upwardly from said second upper surface;
    a hinge operable to pivotably couple said first retractor segment to said second retractor segment, wherein said first retractor segment is pivotable in relation to said second retractor segment between (i) a first relative position in which said first retractor segment lies coplanar with said second retractor segment and forms an access opening therebetween and (ii) a second relative position in which said first lower patient facing surface of said first retractor segment is juxtaposed to said second lower patient facing surface of said second retractor segment;

at least one retractor having a first end portion defining a blade, a second end portion, and an intermediate portion interposed therebetween, wherein (i) said intermediate portion has a plurality of spaced apart bores defined therein, and (ii) each of said plurality of spaced apart bores is configured to receive any of said first plurality of posts and said second plurality of posts; and a locking mechanism operable to lock said first retractor segment and said second retractor segment at any one of a plurality of positions between said first relative position and said second relative position, wherein said locking mechanism includes (i) a first locking member coupled to said first retractor segment and having a first plurality of teeth, and (ii) a second locking member coupled to said second retractor segment and having a second plurality of teeth that mate with said first plurality of teeth.

17. A surgical retractor assembly, comprising:

a first retractor segment having (i) a first upper surface and a first lower patient facing surface, and (ii) a first plurality of posts extending upwardly from said first upper surface;

a second retractor segment having (i) a second upper surface and a second lower patient facing surface, and (ii) a second plurality of posts extending upwardly from said second upper surface;

a hinge operable to pivotably couple said first retractor segment to said second retractor segment, wherein said first retractor segment is pivotable in relation to said second retractor segment between (i) a first relative position in which said first retractor segment lies coplanar with said second retractor segment and forms an access opening therebetween, and (ii) a second relative position in which said first lower patient facing surface of said first retractor segment is juxtaposed to said second lower patient facing surface of said second retractor segment;

at least one retractor having a first end portion defining a blade, a second end portion, and an intermediate portion interposed therebetween, wherein (i) said intermediate portion has a plurality of spaced apart bores defined therein, and (ii) each of said plurality of spaced apart bores is configured to receive any of said first plurality of posts and said second plurality of posts, wherein said first retractor segment defines a first 180° arcuate segment, wherein said second retractor segment defines a second 180° arcuate segment, and wherein said first retractor segment and said second retractor segment collectively form a circle when said first retractor segment and said second retractor segment are in said first relative position.

18. The surgical retractor assembly of claim 17, wherein an upper end portion of each of said first plurality of posts and said second plurality of posts has a slot formed therein that is radially aligned in relation to said circle.

* * * * *